United States Patent [19]

Harrel

[11] Patent Number: 5,547,376
[45] Date of Patent: Aug. 20, 1996

[54] METHODS AND APPARATUS FOR CONTAINING AND RECOVERING ABRASIVE POWDERS FROM AN ABRASIVE POLISHER

[76] Inventor: Stephen K. Harrel, 4510 Ridge Rd., Dallas, Tex. 75229

[21] Appl. No.: 326,763

[22] Filed: Oct. 20, 1994

Related U.S. Application Data

[63] Continuation-in-part of Ser. No. 900,617, Jun. 18, 1992, Pat. No. 5,378,150.

[51] Int. Cl.⁶ .................................................. A61C 1/16
[52] U.S. Cl. .............................................. 433/116; 433/88
[58] Field of Search ................................ 433/82, 86, 88, 433/91, 116, 125; 451/453, 451, 455, 456; 408/67

[56] References Cited

U.S. PATENT DOCUMENTS

| | | |
|---|---|---|
| 2,671,269 | 3/1954 | Francis . |
| 2,703,904 | 3/1955 | De Long ................. 15/372 |
| 2,731,725 | 1/1956 | Wilen . |
| 3,512,258 | 5/1970 | Johnson . |
| 3,522,801 | 8/1970 | Robinson ................. 433/86 |
| 3,526,219 | 9/1970 | Balamuth ................. 128/2 |
| 3,583,821 | 6/1971 | Shaub et al. ............. 451/453 |
| 3,747,216 | 7/1973 | Bassi et al. . |
| 3,786,566 | 1/1974 | Jelicic et al. . |
| 4,061,146 | 12/1977 | Baehr et al. ............. 128/305 |
| 4,111,208 | 9/1978 | Leuenberger ............ 128/305.1 |
| 4,340,365 | 7/1982 | Pisanu ..................... 433/91 |
| 4,428,748 | 1/1984 | Peyman et al. ........... 604/22 |
| 4,634,420 | 1/1987 | Spinosa et al. ........... 604/22 |
| 4,649,919 | 3/1987 | Thimsen et al. .......... 128/305 |
| 4,764,114 | 8/1988 | Jeffcoat et al. ........... 433/72 |
| 4,816,018 | 3/1989 | Parisi ....................... 604/22 |
| 4,917,603 | 4/1990 | Haack ....................... 433/91 |
| 5,122,153 | 6/1992 | Harrel ...................... 433/91 |
| 5,123,903 | 6/1992 | Quaid et al. .............. 604/22 |
| 5,145,367 | 9/1992 | Kasten ...................... 433/91 |
| 5,192,267 | 3/1993 | Shapira et al. ............ 604/22 |
| 5,197,876 | 3/1993 | Coston ..................... 433/116 |
| 5,356,292 | 10/1994 | Ho ........................... 433/88 |

OTHER PUBLICATIONS

Air Polisher Microprophy™ – EX – ad, Danville Engineering (undated).
Crescent Dental Manufacturing Company product advertisement page (undated).
"Microprophy™ Ex Extended Handpiece", Danville Engineering, Inc., (undated).

Primary Examiner—Cary E. O'Connor
Attorney, Agent, or Firm—Richards, Medlock & Andrews

[57] ABSTRACT

A suction attachment for use with an air-driven abrasive polisher to contain an area to be polished and to provide removal of the abrasive powder residue to prevent airborne contamination. A suction attachment body is fixed to the nozzle of the polisher, and is connected to a source of suction to provide a suction influence in the area of polishing. A flexible cover is fastened to the attachment body at one end, and is engaged with the surface to be cleaned at the other end, to enclose and contain the surface area to be cleaned, and provide removal of the abrasive powders via the suction source.

23 Claims, 2 Drawing Sheets

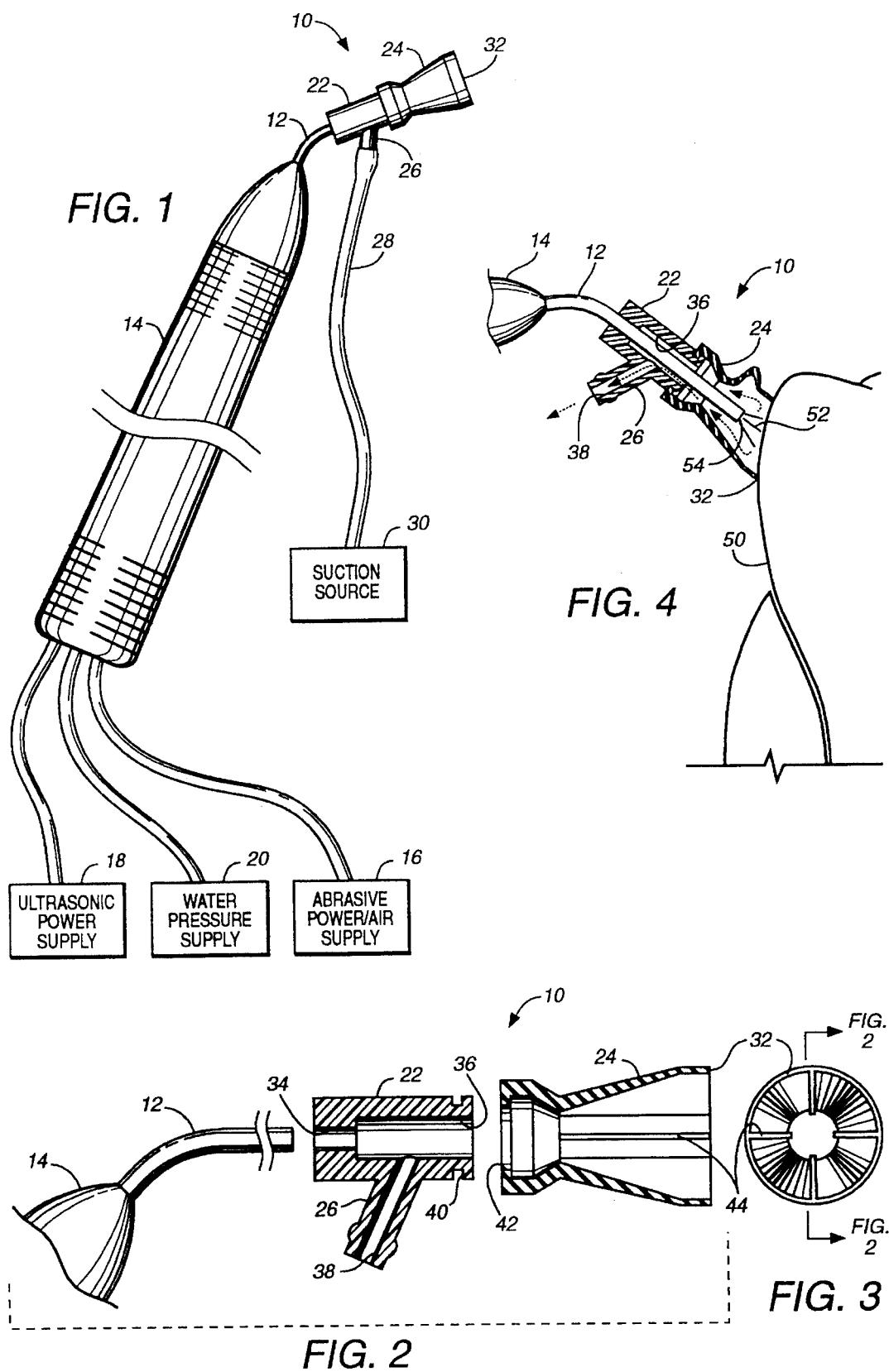

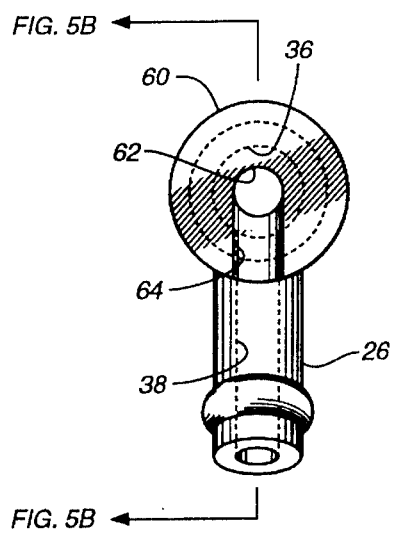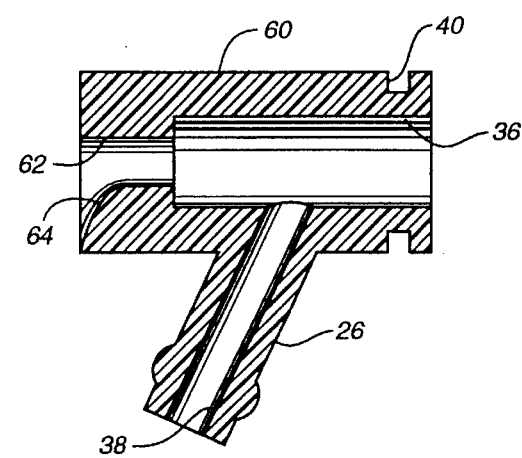
FIG. 5A   FIG. 5B
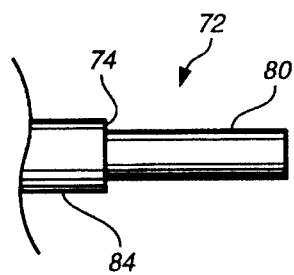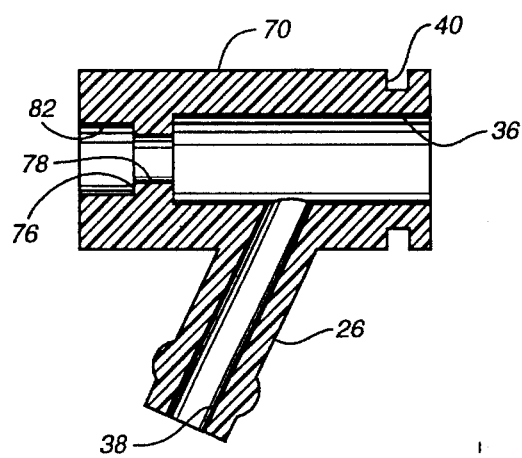
FIG. 6
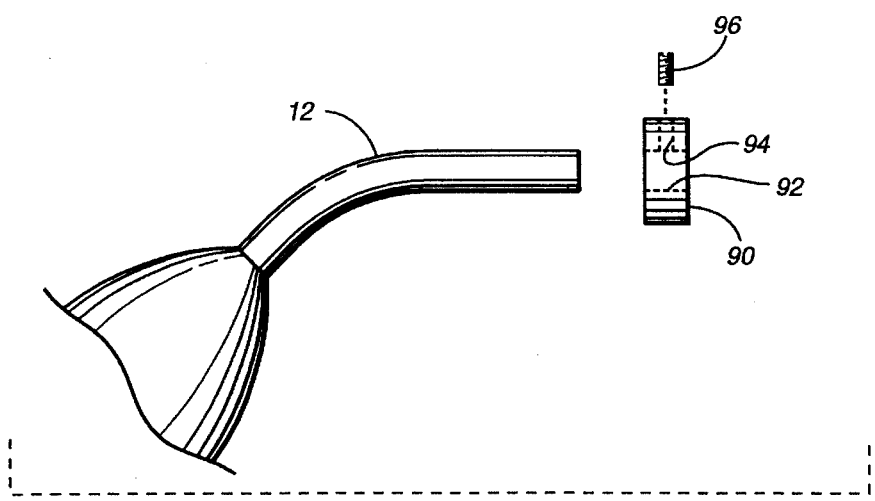
FIG. 7

METHODS AND APPARATUS FOR CONTAINING AND RECOVERING ABRASIVE POWDERS FROM AN ABRASIVE POLISHER

RELATED APPLICATION

This is a continuation-in-part patent application of U.S. Ser. No. 07/900,617, filed Jun. 18, 1992, now issued as U.S. Pat. No. 5,378,150, entitled Method and Apparatus for Controlling the Aerosol Envelope Generated by Ultrasonic Devices, the entire disclosure of which is incorporated herein by reference.

TECHNICAL FIELD OF THE INVENTION

The present invention relates in general to dental polishers and other related equipment, and more particularly to a device attached thereto or made integral therewith for containing the residue of air-driven abrasive powders, thereby reducing the amount of the abrasive powder that becomes airborne and otherwise distributed in the immediate environment.

BACKGROUND OF THE INVENTION

Abrasive-driven polishers are well known in the medical and dental fields for removing undesired deposits from hard tissues, such as teeth, bones, etc. For example, a sodium bicarbonate powder is frequently used as the abrasive medium which is pressurized and directed toward a tooth surface to remove plaque and other types of deposits. In such an operation, air, pressurized to about 30–50 psi, carries the abrasive powder in an air stream that is directed through a small nozzle toward the surface to be cleaned. This forced air stream is pressurized sufficiently to achieve sufficient force to abrade, remove stains and dislodge or wear away the deposits. As can be appreciated, the air-driven abrasive powder is effective to remove the undesired deposits, but is also distributed on nearby surfaces and equipment, as well as becomes airborne. In a typical abrasive cleaning operation, the abrasive powder residue is distributed in the air and leaves a fine layer of powder or dust on everything that is within 10–20 feet of the cleaning operation. The abrasive powder not only provides an unsanitary environment, but such powder can be carried on clothing and footwear as persons leave the area of abrasive cleaning. Further, the airborne powder can carry with it contaminated body fluids, and thus functions as a carrier to contaminate yet other areas by being carried by clothing, footwear, equipment parts, wheeled carts, as well as the ventilation system. The disadvantage of the airborne abrasive powder is thus apparent.

Hand-held abrasive cleaners are readily available which, when connected to a source of air pressure, allow the abrasive powder held in a container to be carried by the air stream and through a nozzle in the end of the hand piece. The instrument can be manipulated so as to direct the air-driven abrasive powder toward the surface to be cleaned. It is mandatory that the dental assistants, as well as the doctor, wear facial masks to prevent inhaling or ingestion of the powder. Other polishers include ultrasonic hand pieces which have an inner, small tubular member for carrying the air-driven abrasive, and an outer tubular member concentric therewith, for carrying a jetted water stream. In the ultrasonic version of the polisher, the water and/or powder jetted from the ultrasonic-vibrating tip is believed to provide a cavitation function for facilitating removal of the deposits with the air-driven abrasive powder. While these and other types of abrasive polishers are well adapted for cleaning hard tissue surfaces, the inherent problems described above have yet to be overcome. Indeed, because of the extreme consequences of air contamination in a hospital environment, such devices are in jeopardy of being discontinued by enforcement of OSHA regulations.

In view of the foregoing, it can be seen that a need exists for a structure that fits on the end of an abrasive polisher to contain the air-driven abrasive powder and prevent the same from becoming airborne. Another need exists for a flexible guard that is fittable on the nozzle of an air-driven polisher, and connectable to a source of suction for containing the abrasive powder to the immediate surface to be cleaned, as well as facilitate the removal of the powder residue, all without substantially interfering with the cleaning operation. Another need exists for a disposable unit that is fittable on the nozzle of a polisher for containing and recovering the powder residue, and which is cost effective so as to be readily disposable.

SUMMARY OF THE INVENTION

In accordance with the principles and concepts of the invention, an attachment is disclosed for use with an air abrasive instrument for containing and collecting the abrasive powder that is left as a residue on the cleaned or polished surface. According to the preferred embodiment of the invention, a suction attachment includes a plastic body having a general cylinder shape with a bore formed in one end thereof for friction fitting onto the tubular nozzle of the air abrasive instrument. A larger diameter bore is formed in the other end of the attachment body to form an annular suction chamber. A suction tube is formed in the sidewall of the attachment body, with a suction bore in communication with the suction chamber. The suction tube is connected to a source of suction by a flexible hose.

A flexible rubber skirt is friction fit on the end of the attachment body such that the suction chamber is essentially extended by the rubber skirting. In a preferred form of the invention, the end of the attachment body includes an external, annular groove in which a rim of the rubber skirt fits to attach the skirting to the attachment body. When the suction attachment is pressed onto the tubular nozzle of an air abrasive instrument, the end of the nozzle is disposed well within the rubber skirting to direct a jet of abrasive powder toward the surface to be cleaned, while the skirting is sealed to the surface to contain the powder residue.

A method of utilizing the suction attachment of the invention is to attach the suction attachment to the nozzle of an air abrasive instrument, and connect the suction tube to a source of suction. The suction attachment, and particularly the annular edge of the rubber skirting, is pressed against the surface to be cleaned, and then the pressurized air-driven abrasive is allowed to be jetted from the nozzle toward the surface. The rubber skirting encloses the area to be cleaned and prevents escape of airborne abrasive residue. Importantly, the source of suction formed in the suction chamber of the attachment body and extended by the rubber skirting, collects the powder abrasive residue after it has been jetted toward the surface to be cleaned. The powder residue is thus contained and recovered and does not contaminate the surrounding environment. In accordance with an important feature of the invention, the air abrasive instrument can be moved along the surface to be cleaned, while the flexible skirt maintains engaged and sealed to the surface to prevent escape of the abrasive powder. Also, the abrasive nozzle can be oriented at various angles with respect to the surface to be cleaned, while the rubber skirting maintains a peripheral engagement with the surface, again preventing escape of airborne abrasive powders.

While a suction is employed in the preferred embodiment, the device will also function without the application of suction to the rubber skirting. In another embodiment, the air pressure itself is employed as the mechanism to carry the abrasive powder to the tooth surface, as well as the mechanism to force the used abrasive from the tooth surface out of an exit tube to a waste container.

BRIEF DESCRIPTION OF THE DRAWINGS

Further features and advantages of the present invention will become apparent from the following and more particular description of the preferred and other embodiments, as illustrated in the accompanying drawings in which like reference characters generally refer to the same or similar elements or functions throughout the views, and in which:

FIG. 1 is a generalized view of the suction attachment of the invention, as attached to the nozzle of an air abrasive instrument;

FIG. 2 is a cross-sectional view of the suction attachment body removed from the flexible skirt;

FIG. 3 is an end view of the open end of the flexible skirt;

FIG. 4 is a cross-sectional view of the suction attachment as utilized with an air abrasive instrument to polish or clean a tooth surface;

FIG. 5 is a cross-sectional view of another embodiment of the suction attachment body that is well adapted for use with an angled nozzle;

FIG. 6 is a cross-sectional view of another embodiment of an attachment body, having an internal shoulder stop engagable with a shouldered nozzle; and FIG. 7 is a side view of a stop member adapted for fastening to a nozzle for providing a stop for the attachment body.

DETAILED DESCRIPTION OF THE INVENTION

The suction attachment device of the invention is well adapted for use with ultrasonic polishers which utilize an ultrasonic tip that jets a mixture of water and air-driven abrasive powders to a surface to be cleaned, as well as the general type of dental or medical polisher which simply uses a nozzle for directing a stream of air-driven abrasive powders to a surface to be polished or cleaned. Of course, the suction attachment described below can be utilized with other types of nozzles carrying abrasive or other types of powders, in which it is desired to recover the residue of the powders and prevent the same from becoming airborne and contaminating the immediate environment.

With reference now to FIG. 1 of the drawings, there is shown the suction attachment 10, as installed on the nozzle end 12 of an air abrasive instrument 14. Typical air abrasive instruments 14 are connected to an abrasive powder/air pressure supply 16 of about 30–50 psi, where the abrasive powder is carried with pressurized air through the instrument 14 to the nozzle 12. Sodium bicarbonate is a typical abrasive powder used in dental polishers. In the case of ultrasonic abrasive instruments, it is connected to an ultrasonic power supply 18 as well as a water pressure supply 20. In the ultrasonic type of air abrasive instruments, the nozzle 12 includes an outer tube carrying a water stream that is agitated by the ultrasonic vibrations to provide a cavitation function to facilitate cleaning of the surface. An inner tube of the nozzle 12 carries the air-driven abrasive powders that are directed under pressure toward the surface to be cleaned. The water carried through the ultrasonic air abrasive instrument also functions to cool the device to remove the thermal energy generated by the ultrasonic-driven mechanism.

The suction attachment 10 includes a body 22 that is suitably attached at one end thereof to a nozzle, and at the other end to a flexible rubber skirt 24. Formed integral with the attachment body 22 is a suction tube 26 that is connected by a hose 28 to a suction source 30. Suction equipment generally available in dental and medical operations is suitable for use as the suction source 30 with the present invention. While not shown, a switch or control can be utilized to manually apply or remove the suction, or adjust the amount of suction applied to the suction attachment 10 during use thereof. Also not shown in FIG. 1, the end of the nozzle 12 projects through the attachment body 22 into the flexible skirting 24. The flexible skirting 24 provides a cylindrical air-tight enclosure when pressed against a surface to contain the air-driven abrasive powders. The residue of the abrasive powders is contained and recovered through the suction tube 26 and collected at the suction source 30. When utilized in conjunction with instruments where water is jetted toward the surface to be cleaned, the powder residue as well as the water and mist is removed via the suction source 30.

FIG. 2 illustrates in more detail the structural features of the suction attachment 10. The attachment body 22 is barrel-shaped and preferably formed of a high density polyethylene plastic. At the nozzle entrance end of the body 22, there is formed a bore 34 having a diameter for friction fitting onto the tubular nozzle 12. A second bore 36 is formed in axial alignment with the first bore 34, but is of a larger diameter than the first bore 34. The second bore 36 is larger than the outside diameter of the nozzle 12 to thereby form an annular suction chamber therearound. The suction tube 26 is formed integral with the body 22 and includes a suction bore 38 that extends through the sidewall of the body 22 and is in communication with the suction chamber defined by the large-diameter bore 36. When a source of suction 30 is connected to the suction tube 26, the suction extends into the annular suction chamber formed by the bore 36, and functions in a manner described below. The body 22 of the suction attachment 10 further includes an annular groove 40 formed at the suction chamber end of the body 22 for attachment of the flexible skirting 24.

The flexible skirting 24 is constructed of a pliable rubber or other type of material to provide a high degree of flexibility thereto. In the preferred embodiment, the flexible skirting 24 includes an inwardly-directed rim 42 for engagement within the annular groove 40 of the attachment body 22. With this construction, the flexible skirting 24 can be quickly affixed and held in an air-tight manner to the attachment body 22, while the peripheral edge 32 of the skirting is sealed against a surface. Such arrangement allows the air abrasive instrument nozzle 12 to be rotated or otherwise moved about to direct or sweep the stream of abrasive powders across the area to be polished. It should be noted that the groove 40 and the rim 42 can be reversed with respect to placement on the attachment body 22 and the skirting 24. The flexible skirting 24 is generally cylindrical in shape, but can be tapered outwardly as shown in FIG. 2, to increase the surface area to be contained. The flexible skirting 24 extends the annular suction chamber formed by the large-diameter bore 36, to the surface to be polished. The flexible skirting 24 also includes an annular peripheral edge 32 for engagement with the surface to be cleaned. Further, the skirting 24 includes a number of inwardly, radially extending webs 44 to provide a certain degree of rigidity, and to prevent collapse of the cylindrical sidewall of the skirting when suction is applied to the attachment device 10.

A flexible skirting member well adapted for use with the invention is obtainable as an attachment to a "Prophy Angle" device, manufactured by Young Dental Manufacturing, located at Earth City, Mo. Another flexible skirting well adapted for use with the invention is obtainable from Crescent Dental Manufacturing Company, Lyons, Ill. The flexible skirting provided with the Prophy Angle device requires removal of the threaded stud therefrom, so that the remaining bore can be enlarged and friction fit onto the end of the attachment body 22. In the other flexible skirting, it must be modified according to the following procedures. A hole can be punched through the portion of the rubber "prophy cup" that is designed to snap fit over the edge of the prophy angle. This procedure will create an annulus for the abrasive tube to extend into the flexible portion of the prophy cup.

When specifically molded for use with the attachment body 22, the flexible skirting 24 can include the rim 42 and the other structure shown in FIGS. 2 and 3. Indeed, those skilled in the art may find that it is preferable to utilize a transparent flexible rubber or plastic so that the operator of the air abrasive instrument 14 can observe the cleaning operation in the area contained by the flexible skirting 24.

With reference to FIG. 4, there is depicted the use of the suction attachment 10 in conjunction with an air abrasive instrument 14 for cleaning or polishing the surface of a tooth 50. The attachment body 22 is shown friction fit to the nozzle 12 to provide an air-tight connection. The nozzle 12 extends through the attachment body 22, with the suction chamber 36 therearound, in communication with the suction bore 38 of the suction tube 26. The operator can press the attachment body 22 onto the tubular nozzle 12 to the extent necessary to place the tip of the nozzle 12 a desired distance from the tooth surface while the flexible skirting 24 engages the tooth. The flexible skirting 24 is urged forward by the instrument 14 so that its peripheral edge 32 engages and seals to the surface of the tooth 50 and provides an enclosed or contained area 52 to prevent escape of the air-driven abrasive powders. The end or tip 54 of the nozzle 12 is spaced a short distance (about 1–3 mm) from the peripheral edge 32 of the flexible skirting 24 to provide working room between the nozzle tip 54 and the tooth surface 50. To that end, the peripheral edge 32 of the flexible skirting 24 can remain engaged and sealed to the tooth surface 50, while the air abrasive instrument 14 and the nozzle 12 is either rotated, swayed or oriented at different angles with respect to the tooth surface 50. Then, before the operator moves the peripheral edge 32 of the skirting 24 to another surface area to be cleaned, the stream of abrasive powders can be interrupted by manually operated controls (not shown), while the suction source still remains in operation to remove the remaining airborne powders or residue within the contained area 52. When the powder residue has been completely removed from the contained area 52, the air abrasive instrument 14 and the suction attachment 10 can be lifted or otherwise moved to another surface area to be polished. It can be seen from FIG. 4 that a circulation path exists from the end of the nozzle 12, to the tooth surface, and back to the suction tube 26. The suction source 30 connected to the suction tube 26 enhances the circulation of spent abrasive powders, for removal and containment at the suction source 30.

The present invention may be readily adapted for use in removing the abrasive powders and aerosol contaminants without the use of suction. In other words, rather than connecting the suction tube 26 to a source of suction, the tube can be connected to a container for collecting the powder and aerosol residue without releasing the same to the atmosphere. In this alternate mode of operation, the pressurized air stream exiting the nozzle 12 is effective not only to abrade the tooth surface with the powder, but also to carry the powder residue and aerosol contaminants through the exit tube 26 to the container. The pressurized air stream creates a circulation path, without the use of suction, from the nozzle 12, to the tooth surface, and then through to exit tube 26 to a container. In this mode of operation, the container would need a filtered opening to the atmosphere to allow a free passage of air to maintain a circulation path, without pressurizing the container, and without releasing the contaminants to the atmosphere. The container itself can be a filter bag or enclosure connected via a tube or hose to the exit tube 26.

FIG. 5 illustrates another embodiment of an attachment body 60. The attachment body 60 is similar to the attachment body 22 described above, but includes a small-diameter bore 62 that has a removed area 64 to accommodate a sharp angle or bend in the tubular nozzle 12 of the air abrasive instrument 14. The removed or cupped area 64 receives the bend or angle of the tubular nozzle and prevents rotation of the attachment body 60 with respect to the nozzle 12. Further, the attachment body 60 is pushed onto the tubular nozzle 12 until the cupped surface of the removed area 64 engages the bend in the nozzle, thereby fixing or seating the parts together. In this manner, the attachment body 60 becomes fixed in position with respect to the nozzle, thus also fixing the end 54 of the nozzle a predefined distance from the peripheral edge 32 of the flexible skirt 24.

In accordance with another embodiment of the invention, FIG. 6 illustrates an attachment body 70 adapted for use with a tubular nozzle 72 that has a shoulder 74. The attachment body 70 includes an inwardly-directed edge 76 providing a stop when engaged with the shoulder 74 of the nozzle 72. The internal edge 78 of the attachment body 70 can be dimensioned to be friction fit on the smaller diameter portion 80 of the nozzle 72. In like manner, the bore 82 of the attachment body 70 can be dimensioned to friction fit with the larger diameter portion 84 of the nozzle 72. With this construction, the suction attachment 70 is friction fit with respect to the nozzle 72 to provide an air-tight engagement, and provides a specified relationship by which the suction attachment 70 can be longitudinally engaged on the shouldered nozzle 72.

Another embodiment of a stop mechanism for positioning the attachment body with respect to the nozzle 12 is shown in FIG. 7. Here, a collar 90, constructed of plastic or other suitable material, is formed with a bore 92 for receiving therein the tubular nozzle 12. A transverse internally threaded bore 94 is formed in the collar 90 for receiving a set screw 96. The set screw can be utilized to fasten the collar 90 to the nozzle 12. In this manner, the suction attachment 22, such as shown in FIGS. 1 and 2, can be installed on the nozzle 12 and abutted against the collar 90. This prevents the suction tube 12 from being pushed through the small-diameter bore 34 of the suction attachment 10 when the instrument 14 is pressed against a surface to be polished.

From the foregoing, disclosed are various embodiments depicting the principles and concepts of the invention. The suction attachment can be economically fabricated of plastic or other suitable material so that it is cost effective, and thus disposable. In like manner, the flexible skirt 24 is also economically constructed and thus is considered disposable. The suction attachment as well as the flexible skirting can be used on a single patient and then disposed. In the alternative, the suction attachment can be sterilized or otherwise cleaned, while the flexible skirting can be used once and disposed of, and a new skirting reattached to the sterilized suction attachment. Further, those skilled in the art may find a suitable material for fabricating the suction attachment integral with the flexible skirting, and formed as a unitary unit. Those skilled in the art may also appreciate that the attachment body of the invention can be made as an integral part of the abrasive instrument nozzle, in which event the flexible skirting is the only disposable element. In this alternative, the air abrasive instrument may be fabricated with an internal suction channel in the instrument that is connected through the nozzle to the annular suction chamber, without the use of the external suction tube and associated hose that are shown in FIG. 1. Also, the attachment body can be formed with an internal annular groove to accommodate an o-ring to seal the unit to the nozzle.

Lastly, the aerosol recovery assembly disclosed in U.S. Pat. No. 5,378,150, by Harrel, entitled Method and Apparatus for Controlling the Aerosol Envelope Generated by Ultrasonic Devices, can be advantageously utilized in conjunction with the present invention. While the abrasive polisher device describe herein will reduce a large percentage of the aerosol contamination, there may be a small percentage of the abrasive lost due to irregularities on the tooth surface or due to spaces between the teeth. In order to capture the small amount of abrasive material that may escape from the flexible skirting, as well as any aerosols of blood or saliva that are generated, the aerosol recovery assembly of the related patent application can also be fitted to the handle of the abrasive polisher. The combination of the abrasive polisher device and the aerosol recovery assembly will eliminate virtually all of the airborne contamination that is produced. Further, when the described invention is used with the aerosol recovery assembly, the suction tube 26 can be attached to the cylindrical body of the aerosol recovery assembly, which then will pull the abrasive powder and other contaminants from the operating site. This arrangement eliminates the need for a separate suction hose.

Thus, while the preferred and other embodiments of the invention have been disclosed with reference to specific structures and functions, it is to be understood that many changes in detail may be made as a matter of engineering choices without departing from the spirit and scope of the invention, as defined by the appended claims. Further, various features or combinations of the apparatus described above can be utilized separately, or together to realize the various individual advantages of the invention.

What is claimed is:

1. Apparatus for use with an abrasive polisher of the type having a rigid nozzle for directing a stream of an abrasive powder toward a surface to be polished, comprising:

an attachment body portion having a bore therein for slidable insertion over the nozzle so as to be supported by said nozzle, said attachment body having an internal chamber, and including a conduit having a bore in communication with the chamber, said conduit being connectable to a container for holding the powder and residue removed from the surface; and a flexible skirting portion connected to the attachment body portion and including a peripheral edge for engaging and containing a surface to be polished, said flexible skirting extending the chamber and providing an enclosed area for containing the abrasive powder, and providing a circulation path for the stream of abrasive powder from the surface through said conduit and to the container.

2. The attachment of claim 1, wherein said attachment body and said flexible skirting are removable from the nozzle.

3. The attachment of claim 2, wherein said attachment body is formed of a rigid plastic and includes a tube formed integral with a sidewall thereof for providing said conduit, and with an opening through the sidewall for connecting the bore of said conduit to the enclosed area of the flexible skirting.

4. The attachment of claim 2, further including a stop mechanism for axially fixing the attachment body with respect to the nozzle.

5. The attachment of claim 1, further including in combination an ultrasonic abrasive polisher having an outer tube carrying a stream of water for providing cavitation action with the abrasive powder.

6. The attachment of claim 1, wherein said attachment body comprises a plastic member having a first end engagable around the nozzle, and a second end for receiving thereon the flexible skirting, and a bore formed from the first end to the second end, and an arm formed integral with the plastic member having the conduit formed in the arm in communication with a chamber formed in the plastic member, and wherein a source of suction is coupled to the conduit in the arm to enhance a circulation path of the abrasive powder for removal thereof.

7. The attachment of claim 1, wherein the attachment body is threadedly engaged with the nozzle.

8. The attachment of claim 1, wherein the attachment body is friction fit to the nozzle.

9. The attachment of claim 1, further including a stop member secured to the nozzle to prevent axial movement of the attachment body along the nozzle.

10. The attachment of claim 1, wherein the flexible skirt is constructed so as to be removably attached to the attachment body and replaced with a new flexible skirt.

11. The attachment of claim 10, wherein the flexible skirt and the attachment body include a groove and lip engagement arrangement for removably fastening the skirt to the attachment body.

12. The attachment of claim 1, wherein the attachment body includes a first axial bore with a diameter friction fittable to the nozzle, and a second axial bore having a diameter larger than the first axial bore, an internal sidewall of said second axial bore being radially spaced from a portion of the nozzle that passes through the first axial bore to thereby define a portion of a chamber.

13. The attachment of claim 1, further including in combination an angled nozzle of the abrasive polisher, and said attachment body includes a cupped portion for receiving a corresponding portion of the angled nozzle to thereby prevent rotation of the attachment body with respect to the angled nozzle.

14. The attachment of claim 1, further including in combination a shouldered nozzle of the abrasive polisher, and said attachment body includes a bore for receiving the shouldered nozzle and an inwardly directed stop formed in the bore for abutting with a shoulder member of the nozzle.

15. The attachment of claim 1, wherein said flexible skirting includes radial webs directed inwardly for providing radial support to prevent collapsing of the skirt when subjected to suction.

16. The attachment of claim 1, further including in combination a source of suction connected to the conduit of the attachment body to facilitate a continuous suction circulation path for removal and containment of the abrasive powders.

17. A suction attachment for use with an abrasive polisher of the type having a nozzle for directing a stream of abrasive powders to a surface to be polished, comprising in combination:

the nozzle being tubular;

a rigid attachment body having a first axial bore with a diameter for inserting the attachment body over the tubular nozzle, a second axial bore being of a diameter greater than the first bore such that an internal sidewall of the second bore is radially spaced from the tubular nozzle which extends through the first bore, said radial space being annular and defining a suction chamber;

a suction conduit formed in said attachment body in communication with said suction chamber, said suction conduit being connectable to a source of suction; and a skirt removably attached to the attachment body so as to be replaceable with a new skirt, said skirt being generally hollow such that said suction chamber is extended into said skirt, said skirt including a flexible peripheral edge engagable with the surface to be polished to provide a confined area influenced by the suction chamber so that abrasive powder residue is removed via said suction chamber to the suction source.

18. The suction attachment of claim 17, further including an arm formed integral with the attachment body, with said suction conduit formed within said arm.

19. A method of polishing a surface with an abrasive powder, comprising the steps of:

fastening a replaceable flexible skirt to an attachment member and fastening the attachment member to an abrasive polisher;

orienting a nozzle toward the surface and directing an air-driven stream of the abrasive powder from the nozzle to the surface;

sealing the nozzle to a portion of the surface to be cleaned with the flexible skirt so as to contain the abrasive powder and prevent escape of airborne powder residue between the flexible skirt and the surface to be cleaned;

circulating the air-driven stream of abrasive powder from the surface to a container to remove the contained airborne powder residue from the flexible skirt; and removing the flexible skirting after use from the attachment member and attaching a new flexible skirting to the attachment member.

20. The method of claim 19, further including applying a suction to the contained area via the attachment member to facilitate the circulation of the abrasive powder.

21. A method of polishing a surface with an abrasive powder, comprising the steps of:

attaching a rigid holder having attached thereto a flexible skirting to an abrasive polisher so that the rigid holder and flexible skirting are carried by the abrasive polisher;

applying a suction to the rigid holder so that the suction exists within the flexible skirting;

directing an air stream from a nozzle carrying the abrasive powder toward the surface to remove deposits formed thereon;

forming an area of suction around an end of the nozzle from which the abrasive powder is directed; and containing and sealing a surface to be cleaned to the nozzle with the flexible skirting so that the contained surface is influenced by the area of suction and so that the nozzle can be oriented at different angles with respect to the surface while maintaining engagement of the flexible skirting to the surface, whereby an abrasive powder residue is removed by way of the suction.

22. The method of claim 21, further including containing the surface to be cleaned by attaching an attachment body to the nozzle, and attaching the flexible skirting to the attachment body so that a volume between the nozzle and the surface to be polished is contained and air-tight.

23. Apparatus for use with an abrasive polisher of the type having a nozzle for directing a stream of an abrasive powder toward a surface to be polished, comprising:

an attachment body fastenable to the nozzle and providing an internal chamber, and including a conduit connected to the chamber, said conduit being connectable to a container for holding the powder and residue removed from the surface; and a flexible skirting removably attached to the attachment body by way of a groove and lip engagement, and wherein said flexible skirting includes a peripheral edge for engaging and containing a surface to be polished, said flexible skirting extending the chamber and providing an enclosed area for containing the abrasive powder, and providing a circulation path for the stream of abrasive powder from the surface through the conduit and to the container.

* * * * *